United States Patent [19]

Lichtman

[11] Patent Number: 5,318,589
[45] Date of Patent: Jun. 7, 1994

[54] SURGICAL INSTRUMENT FOR ENDOSCOPIC SURGERY

[75] Inventor: Philip R. Lichtman, Newton, Mass.
[73] Assignee: Microsurge, Inc., Needham, Mass.
[21] Appl. No.: 869,535
[22] Filed: Apr. 15, 1992
[51] Int. Cl.⁵ ............................................. A61B 17/32
[52] U.S. Cl. .................................. 606/205; 606/167; 128/751
[58] Field of Search ............ 606/51, 52, 83, 174, 606/205–211, 167, 170; 128/750–755

[56] References Cited

U.S. PATENT DOCUMENTS

| | | |
|---|---|---|
| 3,404,677 | 10/1968 | Springer . |
| 4,393,872 | 7/1983 | Reznik et al. . |
| 4,427,014 | 1/1984 | Bel et al. ............... 128/751 |
| 4,712,545 | 12/1987 | Honkanen . |
| 4,896,678 | 1/1990 | Ogawa ................. 128/751 |
| 5,026,370 | 6/1991 | Lottick . |
| 5,026,375 | 6/1991 | Linovitz et al. . |

*Primary Examiner*—Stephen C. Pellegrino
*Assistant Examiner*—William W. Lewis
*Attorney, Agent, or Firm*—Pandiscio & Pandiscio

[57] ABSTRACT

A surgical instrument is provided that comprises two coaxial tubes mounted for relative telescoping motion, and a unitary jaw piece of springy material affixed to the remote end of one of said tubes and having two jaws normally biased apart to a selected open position. The other one of said tubes is movable longitudinally relative to said one tube so that the forward end of the said other tube forces the jaws to close. The jaw piece includes a body section joined to the two jaws by spring leaves having a selected configuration, with the result that when the jaws are moved to closed position, the forward ends of the jaws engage one another before there is any engagement between the rear ends of the jaws. The jaw piece also has an opening permitting introduction of an ancillary device to a position permitting communication with the space between the jaws.

30 Claims, 6 Drawing Sheets

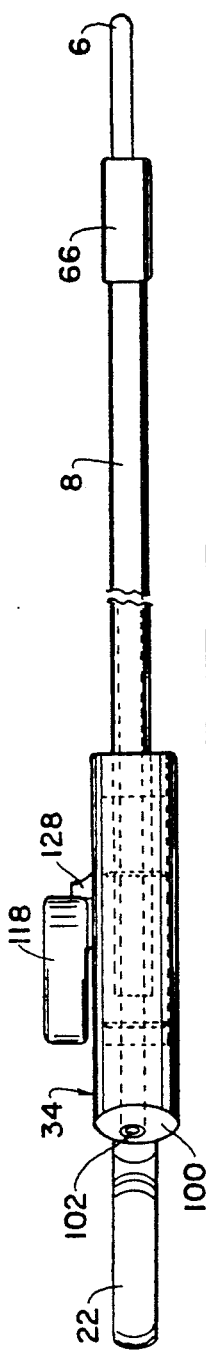
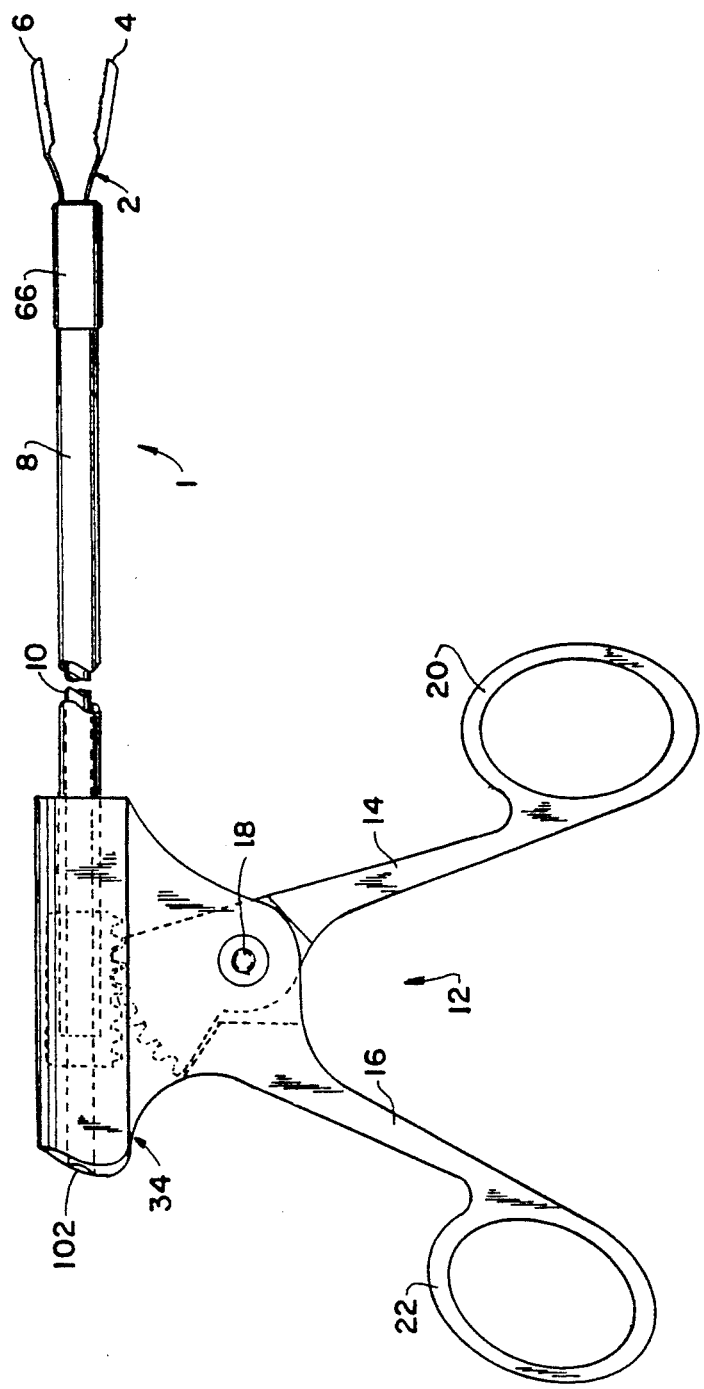

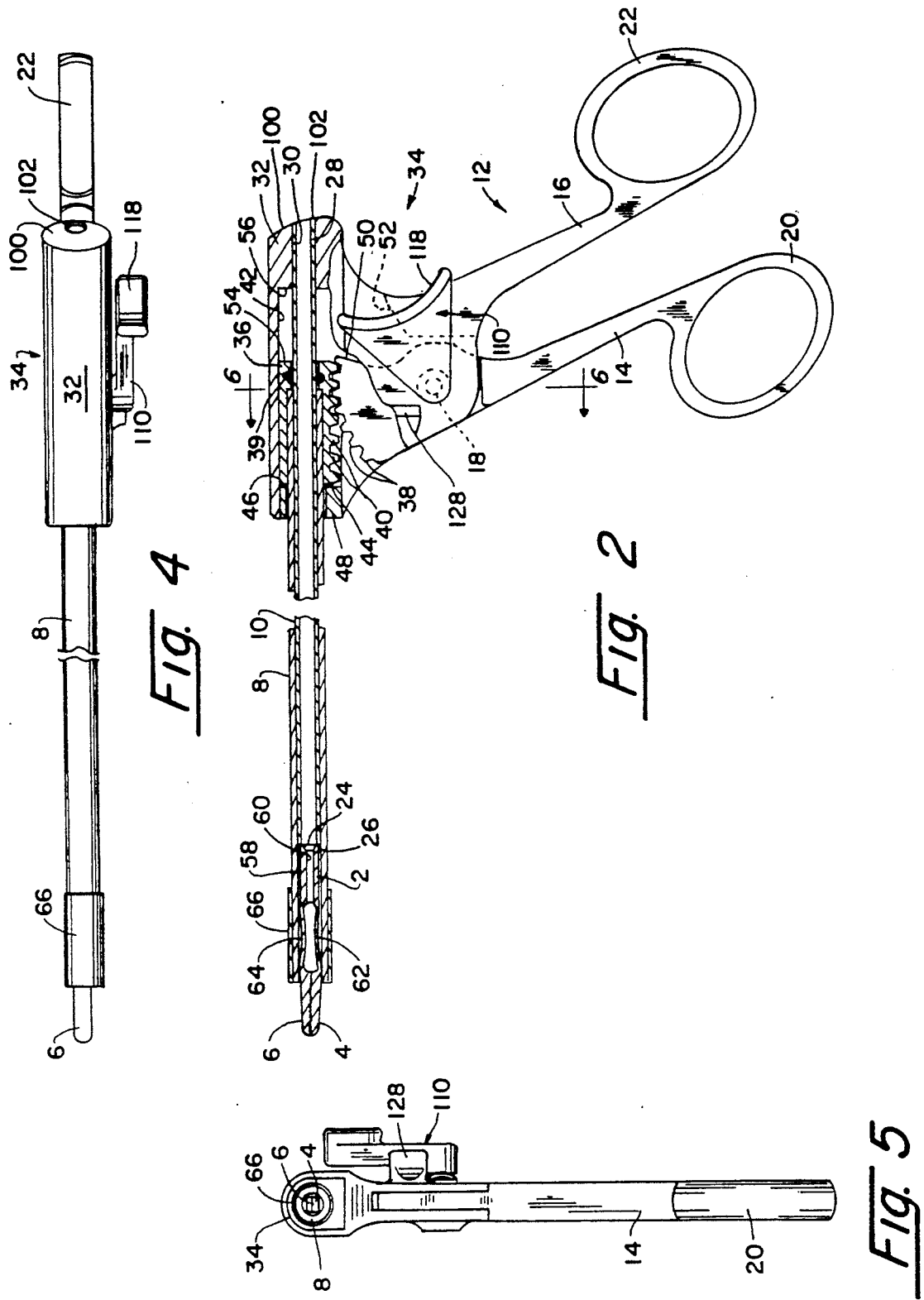

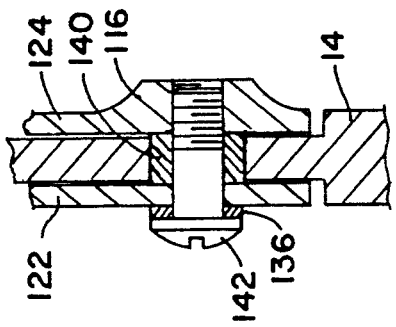
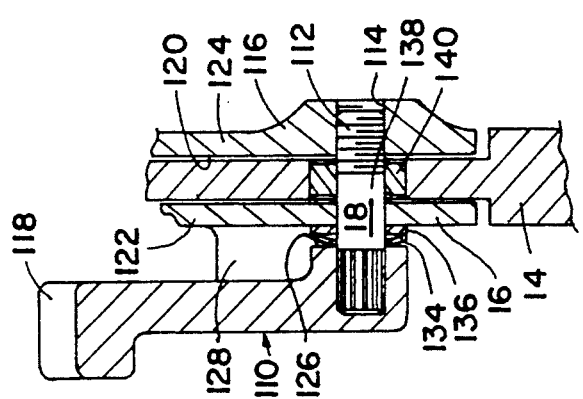
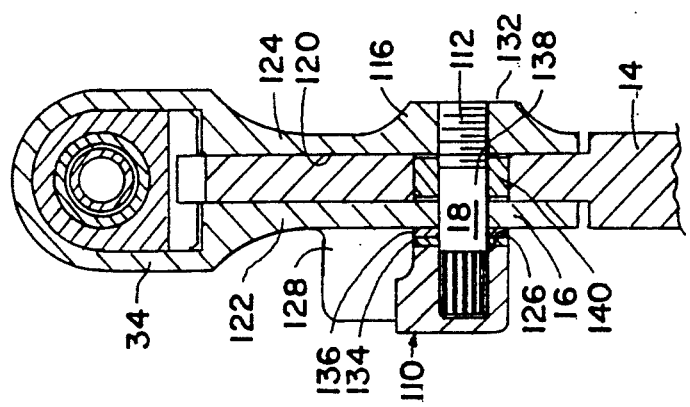

SURGICAL INSTRUMENT FOR ENDOSCOPIC SURGERY

FIELD OF THE INVENTION

This invention relates generally to a surgical tool or instrument for use in endoscopic surgery which is especially useful for grasping, cutting, or otherwise remotely manipulating bodily tissues during surgery; and is more particularly concerned with such a tool in which an unobstructed longitudinal bore or channel is provided so as to permit another surgical instrument, such as a fiber optic light guide or other ancillary device, to be passed between operating jaws of the tool for purposes of irrigating, visualizing, or further manipulation of the tissues.

BACKGROUND OF THE INVENTION

Surgery frequently requires the grasping or cutting of tissues and organs situated at some distance from the surgeon's hand, such as within a body cavity. In particular, endoscopic surgery often requires that the surgical site be a substantial number of centimeters from the initial incision. In endoscopic surgery, relatively small incisions are made by means of a trocar. The work is observed by means of a slender optical device (endoscope) inserted through a small incision into which a cannula may be placed. Endoscopic techniques, which are minimally invasive and relatively non-traumatic, are displacing conventional open surgery for many procedures, and instruments for endoscopy are proliferating.

A typical instrument employed in endoscopic surgery has a pair of articulated jaws, and a handle mechanism comprising two members, one movable with respect to the other, which can conveniently be manipulated so as to cause the jaws to open and close. Serrations, blades, or other features (depending upon the use for which the tool is intended) enable the jaws to perform various surgical functions, such as grasping or cutting. The articulated jaws are located at the distal end of a relatively long extension of the handle mechanism. The length of the shaft extension is determined by the depth of the surgical site, while its cross-sectional dimensions are established by the maximum permissible incision size.

Many ingenious linkages have been devised for converting the surgeon's manual efforts at the handle end of the instrument into opening and closing of the tool's jaws. Typically, although with some exceptions, the handle has a stationary member rigidly joined to a hollow shaft and a movable member pivotally attached to an operating rod that is mounted and is capable of reciprocal movement within the shaft. When the surgeon squeezes the stationary and movable handle members together, the operating rod acts upon the jaws (to which it is rotatably fastened by pins, or by tracks or levers kinematically equivalent to pins) in such a way as to make the jaws close. When the surgeon spreads the stationary and movable members apart, the motions are reversed and the jaws open. The jaws are rotatably attached to the end of the shaft by known means, e.g., by pins or kinematically equivalent tracks. In some cases, levers or other intermediate pieces are interposed between the operating rod and the jaws for causing the latter to open and close in response to relative movement of the stationary and movable handle members.

Although their constructional details and relationships to each other vary widely, such pins, tracks, levers, and other connecting components tend to preclude the presence, or limit the size, of a bore in the instrument through which an ancillary device, e.g., a fiber optic light guide, may be introduced adjacent to or between the jaws. These components cannot be miniaturized without limit, for reasons of strength; nor can they be relocated without disturbing the critical geometry of the linkages. Furthermore, it is not advisable to increase the shaft's diameter, which would necessitate a larger incision and detract from the benefits of the endoscopic method.

When operating the jaws of typical tools as described above, surgeons have experienced difficulty in grasping slippery tissues because the jaws close first at their rear ends and thereby tend to propel or push the tissues out from between the jaws. Consequently trauma of the tissues may result from repeated and increasingly aggressive attempts to grasp the tissue.

OBJECTS OF THE INVENTION

The primary object of the present invention is to provide the surgeon with a tissue-manipulating instrument which is relatively atraumatic.

A further object of the invention is to provide a tissue-manipulating instrument having a bore or channel through which useful ancillary devices, such as a laser-conducting fiber optic light guide or another surgical instrument can be conveyed so as to make contact or near-contact with the tissues being grasped, cut, or otherwise manipulated.

Another object is to provide a tissue-manipulating instrument for endoscopic procedures having a bore or channel extending through the instrument to permit irrigation or aspiration through said bore or channel, without the need for a separate cannula.

Yet another object is to provide a tissue manipulating surgical instrument having the capability of working around corners; that is, the instrument may be curved along the length of its shaft so that the axis of motion of its jaws is offset from the proximal end of the shaft (i.e. the end of the shaft attached to the handle mechanism is displaced laterally from the plane of engagement of the jaws where the jaws are used to grasp, incise or dissect tissue).

Still another object is to provide an instrument for endoscopic procedures having a bore or channel extending longitudinally therethrough for accommodating and supporting an endoscope. The instrument is effectively a sheath for the endoscope, so that the tissues being manipulated can be visualized from close up, and in some procedures making possible the elimination of a separate incision for the endoscope.

A further object of the invention is to combine, in one instrument, the grasping action of serrated jaws with the cutting action of a laser, so that the endoscopic removal of tissues is facilitated.

Another specific object is to provide a surgical instrument of the character described comprising tissue-manipulating jaws and manually-operated means remote from said jaws for causing said jaws to open and close in a predetermined manner.

Still further objects of the invention include providing an improved surgical instrument for the endoscopic procedures which may take the form of incisors, scissors, dissectors, forceps, cauterizers or needle holders.

SUMMARY OF THE INVENTION

In a preferred embodiment of the invention, a surgical instrument for endoscopic procedures is provided having a jaw subassembly comprising two opposing jaws which are made from a single piece of springy material, with the integral jaw subassembly being formed so that the jaws are normally biased to a wide open position. The jaw subassembly is housed partially within a tube which is operatively movable longitudinally of the instrument by the movable member of an instrument handle. By squeezing together the moving and stationary members of an instrument handle, the surgeon can cause the tube to override or envelop a portion of the two jaws. Since the jaws normally diverge at a considerable angle, and since their end separation is much greater than the diameter of the tube, movement of the tube forward toward the jaws forces the jaws together in the manner of a collet. Reversing the motion of the handle enables the springy jaws to open again. This arrangement causes the jaws to grasp the tissue immediately upon being brought together without propelling or pushing the tissue being addressed out from between the jaws.

Because the one-piece jaw assembly requires no articulation, thereby eliminating pins, levers, tracks, and other potential obstructions, there is room for an axial bore which extends completely through the instrument and through which may pass, completely unimpeded, fiber optic light guides, lasers, cauterizing means, surgical tools, endoscopes, and other surgical devices. These auxiliary devices can traverse the space between the jaws and project beyond them, so as to touch the tissues between or ahead of the jaws. The axial bore also can conduct fluids to and from the tissues, e.g. for aspiration or irrigation purposes.

An optional locking means enables the surgeon to lock the handle members in any relative position within their range of motion, and consequently to lock the jaws in any position to which they have been moved.

BRIEF DESCRIPTION OF THE DRAWINGS

These and other advantages will become more readily apparent upon a reading of the detailed description following hereafter and upon an examination of the drawings, in which like parts are identically numbered, and in which:

FIG. 1 is a right-hand side view in elevation of a preferred embodiment of the surgical apparatus of the invention, partially in phantom, showing the jaws wide open and, correspondingly, the handle members spread as far apart as possible;

FIG. 2 is a left-hand side view in elevation of the preferred embodiment shown in FIG. 1, partially in longitudinal cross-section through the shaft axis, showing the jaws completely closed and, correspondingly, the handle members squeezed together as far as possible, and also showing the locking lever in its fully locked position;

FIG. 3 is a plan view of the preferred embodiment, partially in phantom, with the jaws wide open and the locking lever in its fully unlocked position;

FIG. 4 is a plan view of the preferred embodiment, with the jaws fully closed and the locking lever in its fully locked position;

FIG. 5 is a front end view in elevation of the same preferred embodiment, with the jaws fully closed and the locking lever in its fully unlocked position;

FIG. 6 is a partial cross-sectional view taken along line 6—6 of FIG. 2, but showing the locking lever in its fully locked position;

FIG. 7 is a partial cross-sectional view similar to FIG. 6 but showing the locking lever in its fully unlocked position;

FIG. 8 is a fragmentary cross-sectional view, similar to FIG. 7, of another embodiment in which the lock has been eliminated altogether and the apparatus is permanently unlocked;

DETAILED DESCRIPTION OF THE INVENTION

Figure 11:
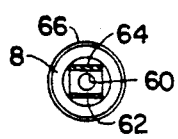
FIG. 11 is a cross-sectional view taken along line 11—11 of FIG. 10.

As shown in FIGS. 1-5, the instrument of the invention 1 in its preferred embodiment is seen to comprise a jaw piece 2 divided at its front end into two or more jaws 4 and 6; an outer tube 8, inside of which resides an inner tube 10; and a stationary housing 34 having a handle 12. The latter includes a movable handle member 14 that is rotatable with respect to a stationary handle member 16 about a pivot pin 18. Handle member 16 is formed integral with or fixed to housing 34. Operation of the handle members is facilitated by a finger loop 20 on movable handle member 14 and a finger loop 22 on stationary handle member 16. Other means of grasping and manipulating movable member 14 and stationary member 16 may be provided. For example, stationary handle member 16 can take the shape of a pistol grip and movable member 14 may be a trigger, the two members being spring loaded apart so that only contractile hand motions are required of the surgeon to close the jaws, obviating the need for finger loops.

As seen best in FIG. 2, jaw piece 2 is shown to be rigidly connected to and spaced from stationary handle member 16 by inner tube 10, such as by welding the rear end face 23 of jaw piece 2 to the front end 26 of inner tube 10. The rear end 28 of the inner tube 10 is secured in a bore 30 formed in barrel portion 32 of the stationary housing 34 by a press fit or other suitable means.

With further reference to FIG. 2, outer tube 8, which is coaxial with and freely fitted over inner tube 10, is rigidly joined to a gear rack 36 such as by press fitting or molding. Outer tube 8 and gear rack 36 slide freely relative to inner tube 10. An O-ring 39 is provided in a groove in gear rack 36 so as to be in sliding engagement with tube 10, whereby to prevent leakage of fluid into the cavity 42, and therefrom to the atmosphere. Movable handle member 14 is provided with gear teeth 38 which engage gear teeth 40 of gear rack 36. When movable handle member 14 is rotated about the axis of its pivot pin 18, the meshing of gear teeth 38 and 40 causes gear rack 36 to translate axially in cavity 42 of barrel portion 32 of stationary housing 34. Other means may be employed for causing gear rack 36 to translate within cavity 42. For example, a single tooth or peg might extend radially from movable handle member 14 and engage a single transverse slot in gear rack 36 to effect translation of gear rack 36 within cavity 42.

Figure 9:
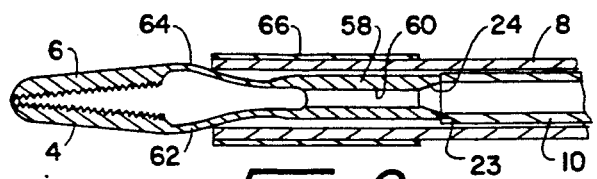
FIG. 9 is a longitudinal sectional view in side elevation of the tip (or jaw end) portion of the preferred embodiment shown in FIG. 2, except that the jaws are shown incompletely closed, contact between them having just been initiated at the remote outermost end of the jaws.

As gear rack 36 translates within cavity 42, outer tube 8 translates identically since the two parts are securely joined together. Since jaw piece 2 is rigidly attached to stationary handle member 16 via inner tube 10, jaws 4 and 6 remain at a fixed distance from stationary handle member 16. By contrast, outer tube 8 moves axially toward or away from stationary handle member 16 as gear rack 36 is forced to reciprocate within cavity 42 by the rotation of movable handle member 14 with respect to stationary handle member 16. Thus, outer tube 8 can override or envelop jaws 4 and 6 to a degree that depends on the relative lengths of outer tube 8 and inner tube 10, and the relative rotational positions of movable handle member 14 and stationary handle member 16. These relative rotational positions are limited in the contractile direction (as shown in FIG. 2) by the abutting of the front end 44 of gear rack 36 against the rear face 46 of a plug 48. Plug 48 is tightly secured in the front end of cavity 42 and establishes the forward termination of cavity 42. In the extensile direction (as shown in FIG. 9) the relative rotational limit positions of the handle members 14 and 16 are reached when an edge surface 50 (see FIG. 2) of movable handle member 14 abuts surface 52 within stationary housing 34. As indicated in FIG. 2 an alternative limit position could be achieved by rear face 54 of gear rack 36 contacting a surface 56 that terminates cavity 42 within barrel 32 of housing 34.

Figure 10:
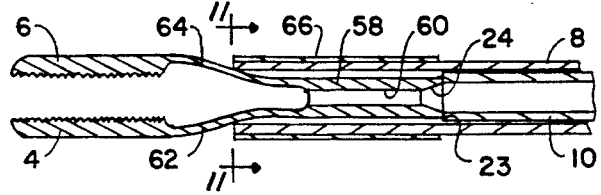
FIG. 10 is a longitudinal sectional view similar to FIG. 9 except that the jaws are shown partially opened in an intermediate position.
Figure 12:
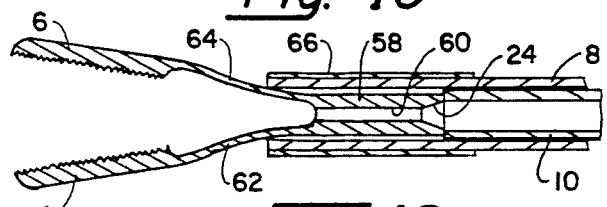
FIG. 12 is a longitudinal sectional view in side elevation, similar to FIG. 9, except that the jaws are shown fully opened.

FIGS. 12, 10, and 9 and the like portion of FIG. 2 depict in sequence the relative orientation of jaws 4 and 6 from fully open to fully closed position. Jaw piece 2 has three distinct sections. A rear section 58 is attached rigidly, as described above, to the front end of inner tube 10. Rear section 58 (see FIG. 9) has an axial hole 60 extending therethrough beginning at the rear end face 23, and preferably the rear end of hole 62 is tapered as shown at 24. Ancillary devices may pass through this hole 60 via inner tube 10, with insertion thereof being assisted by the taper 24. Forward of rear section 58, jaw piece 2 divides into two (as shown) or more flexible cantilevered leaves 62, 64, which comprise the center section of jaw piece 2.

Still further forward of rear section 58, the leaves 62, 64 thicken into the form of relatively inflexible jaws 4 and 6, the latter forming the front section of jaw piece 2. Jaws 4 and 6 are shown in FIGS. 2, 9, 10 and 12 as being serrated for purposes of grasping tissues securely. However, jaws 4, 6 can assume many other shapes, e.g., they may be smooth, tapered, grooved, and/or toothed. It should be observed that in their unrestrained state (FIG. 12), leaves 62, 64 diverge from rear section 58 at a substantial angle. Because of the angle of divergence between leaves 62 and 64, there is a considerable gap between jaws 4 and 6 in their free state, particularly at their forwardmost ends. This gap is sized to admit a suitable thickness of tissue for being grasped or otherwise manipulated.

Leaves 62, 64 are long enough and thin enough to be elastically flexible over the range of motion depicted sequentially in FIGS. 12, 10, 9 and 2. The length and thickness of leaves 62 and 64 must be carefully dimensioned since the proper functioning of the apparatus is strongly dependent upon proper selection of these parameters. It should be noted that leaves 62 and 64 are not straight. In their free state, as shown in FIG. 12, leaves 62, 64 are seen to arc in a convex manner away from each other where they join rear section 58. Just rearward of the junction of leaves 67 and 64 with jaws 6 and 4, however, leaves 62, 64 undergo an inflection so as to arc in a concave manner toward each other.

Leaves 62, 64 are sufficiently wide, as viewed normal to their thickness (see FIG. 11), to resist strongly any lateral deflection, that is, deflection transverse to the plane of FIG. 2. If the leaves 62, 64 are made of a metal such as steel, they are heat treated so that they will not deform plastically, even if forced open considerably more than is shown in FIG. 12. However, leaves 62 or 64 are not so hard or brittle that they are prone to fracture if so deformed. It should be noted that the jaws 4 and 6 can be so formed that one of them is connected to rear section 58 by a leaf 62 or 64 as described above, while the second leaf may be thicker and hence stiffer or more inflexible all the way to its junction with rear section 58, with the result that the thick-leaved jaw remains relatively motionless even when the thin-leaved jaw deflects as shown in FIGS. 12, 10, 9, and 2. If desired, multiple pairs of jaws may be provided, with all of the jaws having flexible spring leaf sections 62,64, or one or more pairs of jaws 4 being attached to relatively inflexible spring leaf sections, and one or more pairs of jaws 6 being attached to relatively flexible spring leaf sections.

Jaw piece 2 can be fabricated from a piece of square-section spring steel or a steel blank of round cross section, in which case it might be split into three or more jaws, instead of the two opposed jaws shown in the drawings.

Figure 14:
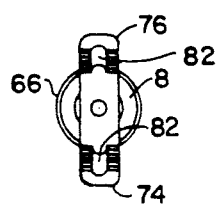
FIG. 14 is a front end view of the embodiment of FIG. 13.
Figure 13:
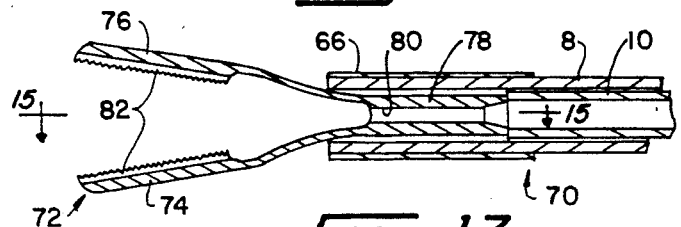
FIG. 13 is a sectional view like FIG. 12 of a further embodiment of the invention, with the jaws having centrally located grooves that permit the passage of an ancillary device even when the jaws are fully closed.
Figure 17:
FIG. 17 is a plan view of the embodiment of FIG. 16.
Figure 15:
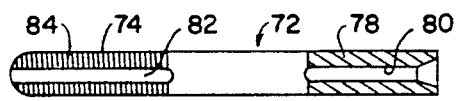
FIG. 15 is a longitudinal cross-sectional view, taken along line 15—15 of FIG. 13 showing details of one of the jaws.
Figure 16:
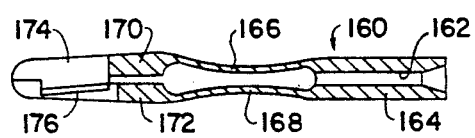
FIG. 16 is a longitudinal sectional view of the jaw end of a further embodiment of the invention wherein a cutting blade is provided.
Figure 20:
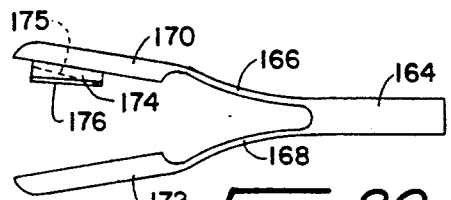
FIG. 20 is a side view of the embodiment of FIG. 16 showing the jaws wide open.
Figure 18:
FIG. 18 is a bottom view of the embodiment of FIG. 16.
Figure 19:
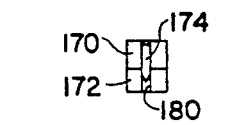
FIG. 19 is a front end view of the embodiment of FIG. 16, indicating the fully closed position of the jaws and cutting blade.

As shown in FIGS. 13, 14, and 15 the instrument of the invention may provide for the insertion or passage of ancillary devices, even with the jaws in closed position. An instrument 70 (FIG. 13) is provided with a jaw piece 72 comprising jaws 74 and 76 and a rear section 78 which is provided with an axial hole 80 in alignment with the interior of inner tube 10. The jaws are grooved axially as shown at 82 in FIGS. 14 and 15 so that even when they are completely closed, an ancillary device can be inserted between them. Passage of an ancillary device through tube 10, hole 80 and grooves 82 is thus made possible, even when the jaws are fully closed. This is essential in the case where jaw piece 72 has one leaf that is substantially thicker and hence stiffer than the thinner leaf of the other jaw, to prevent the relatively inflexible thicker leaf or leaves from impeding the passage of an ancillary device into the center section of jaw piece 72 even when jaws 74, 76 are open. Serrations 84 may be provided on the jaws to aid in gripping tissue.

Where it is desired to provide an instrument that enables the cutting or dissecting of tissue, an embodiment as shown in FIGS. 16–20 may be employed. In this arrangement a modified jaw piece 160 (FIG. 16) is provided. This jaw piece 160 is substantially identical to the jaw piece 2 of the embodiment of FIG. 2 in that it is formed with an axial hole 162 through the rear section 164, and the latter is connected by means of cantilevered leaves 166 and 168 to the jaws 170 and 172, respectively (FIGS. 16 and 20). In the position where the jaws are fully opened (FIG. 20) any ancillary device may pass through the hole 162 and between the jaws 170, 172 as in the previously described embodiments. However, in this embodiment, the jaws are provided with cutting means. A cutting blade 174, having a sharpened cutting edge 176, is mounted within a slot 178 (FIG. 17) located in jaw 170. Blade 174 is fixed in slot 178, e.g., by welding, so that the blade remains fixed to jaw 170 during operational use. Jaw 172 is provided with a slot 180 having a width slightly greater than the thickness of blade 174 so as to enable easy manipulation of the blade into and out of the jaw piece 172 while promoting a suitable cutting action. Because of the ability to flex the leaves 166, 168, the jaws 170, 172 may be closed against one another (see FIG. 16) when the sleeve or outer tube 8 (see FIG. 2) is fully extended. The jaws 170, 172 may be so dimensioned that the final closing, as brought about by positioning outer tube 8 from the position of FIG. 9 to that of FIG. 2, will cause the cutting edge 176 of blade 174 to move into slot 180 so as to cut through the tissue being addressed. Additionally, a blade 174 larger than that shown in FIG. 16 may be used which projects forward beyond the front end of lower jaw 172, if desired, so that the instrument may be used for making an incision. A further option is to design blade 174 so that its leading edge is closer to jaw 170 than its rear or trailing edge (as shown in dotted lines 175 in FIG. 20), whereby when the jaws are brought partly into closing relation the rear end of the cutting blade will close first onto the lower jaw 172, whereupon the surgeon may extend the instrument forward to slit interfering tissue, in a manner similar to a paper slitter.

Figure 23:
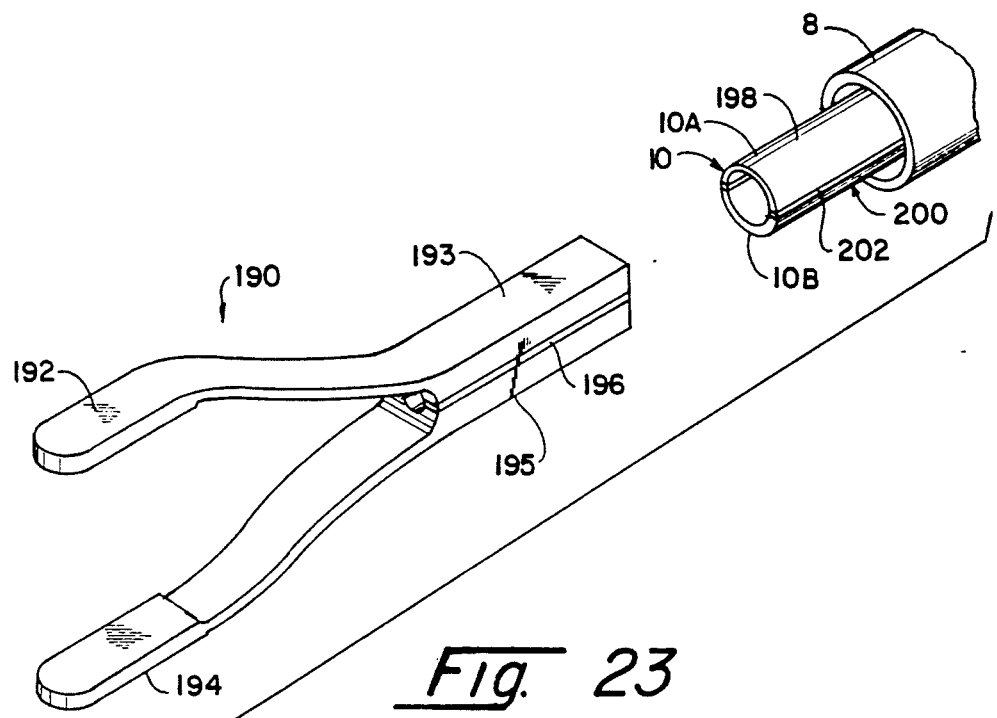
FIG. 23 is an exploded perspective view of the tip portion of a further embodiment of the invention for use in bi-polar electrosurgery.

It should be noted that the instrument may be adapted for monopolor electro-surgery, simply by connecting an appropriate source of electrical power to inner tube 10. Where it is desired to provide an instrument for bipolar electrosurgery, the embodiments shown in FIGS. 23 and 24 may be employed. In one such arrangement (FIG. 23) a jaw piece 190 of conductive material such as spring steel may be provided. However, in this embodiment, the jaw piece 190 comprises separately formed jaws 192, 194. The latter are affixed to the inner tube 10 and insulated from one another by an intervening non-conductive strip 196 extending between and preferably bonded to the rear sections 193 and 195 of jaws 192 and 194 respectively. In this embodiment it is preferred that inner tube 10 be a split conductive tube comprising opposed sections 10A and 10B separated by an insulation strip 202 as shown in FIG. 23, with tube 10 being made of electrically conductive material. With the foregoing arrangement, separate electrical connections may be made to conductive jaws 192 and 194 via sections 10A and 10B of tube 10, whereby the two jaws may serve as electrodes. If the tube 10 is made of a non-conductive material, the electrical connections to jaws 192, 194 may constitute conductors (not shown) embedded in the inner tube 10 which extend to the distal end of tube 10 and are brought into electrical contact with the rear section 193, 195 of jaws 192, 194, respectively.

Figure 24:
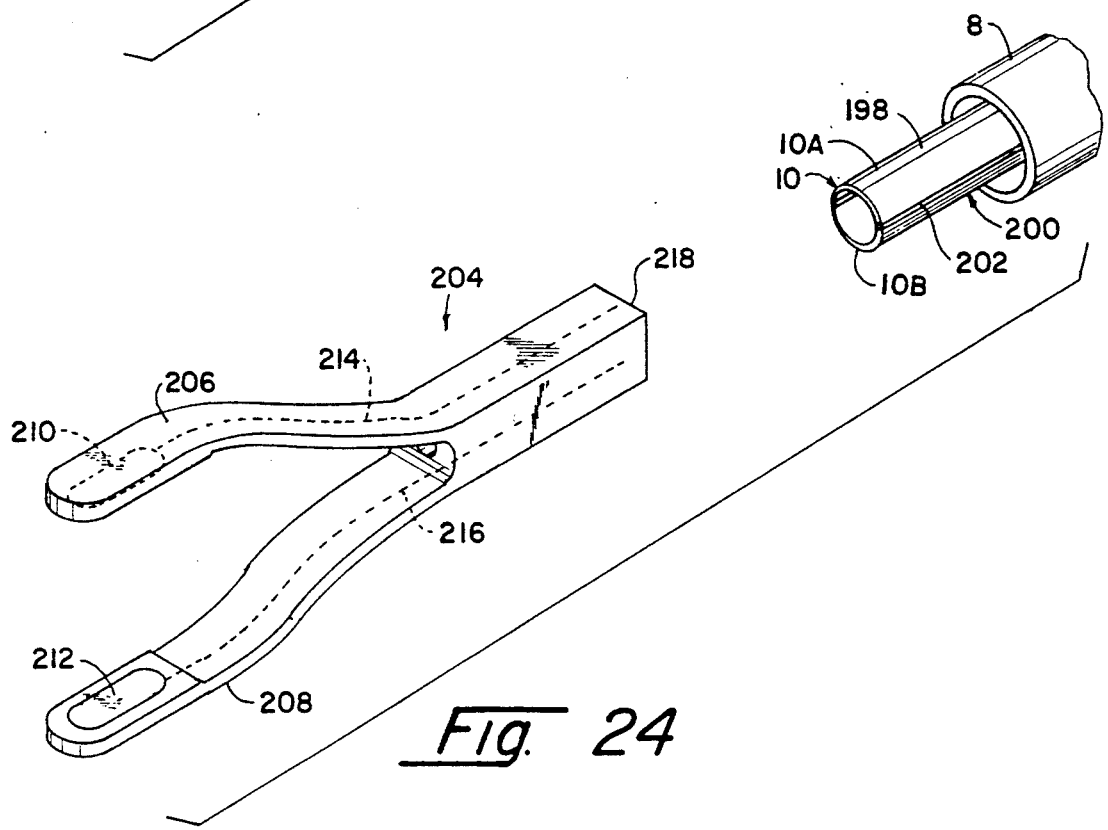
FIG. 24 is an exploded perspective view of the tip portion of a still further embodiment of the invention for use in bi-polar electrosurgery.

In a further embodiment of an instrument for use in electrosurgery (see FIG. 24) a jaw piece 204 of non-conductive material is provided. This can be a one-piece unit characterized by a degree of springiness which keeps the jaws 206, 208 normally spread apart as shown in FIG. 24. Electrodes of any desired shape, including simple wires or the "shoes" 210 and 212 as shown, are embedded within the jaws 206, 208, respectively. Conductor strips 214, 216 lead from the electrodes 210, 212, respectively, through the rear end 218 of the jaw piece, where they are mated with the two sections 10A and 10B of inner tube 10 in a suitable electrical connection.

In operation of the preferred embodiment shown in FIGS. 1–5, assuming that the surgeon desires to grasp a bit of tissue between jaws 4, 6, which are wide open as shown in FIG. 12, he positions jaws 4, 6 so that the tissue lies between them and then squeezes movable handle member 14 toward stationary handle member 16, thereby causing outer tube 8 to translate toward jaws 4, 6 and commence to slide over or envelop them. As this envelopment proceeds, jaws 4, 6 are forced to close, precisely like a collet, so as to grasp securely the tissue between them. FIG. 10 shows the jaws 4 and 6 partially closed, as occurs on initial movement of handle member 14 toward stationary handle member 16. Upon further motion of the handles, as shown in FIG. 9, jaws 4, 6 have closed to the extent that their tips touch. Still further motion of the handles will result in closing the jaws substantially fully, as seen in FIG. 2. However, as explained hereafter, this does not necessarily imply that the tissues being manipulated have been mashed flat when the jaws are in the position shown in either FIGS. 9 or 2. In this connection, it is to be appreciated that the closing of jaws 4 and 6 is progressive, starting with engagement of only their forward ends and then progressing so as to cause the rear ends of the jaws to make contact with the tissue last, except where relatively thick tissue is being grasped, in which case the jaws may not be parallel or nearly so, but instead may be in a partly open position while still grasping the tissue.

It is clear that the design geometry of jaws 4, 6 can be varied a great deal, so as to accelerate or retard the rate of closure of jaws 4, 6 as a function of the relative positions of handle members 14 and 16. Also, in order to manipulate different types of tissues, the jaws may be configured for differing force distributions along the lengths of jaws 4, 6.

It is to be noted that the gap between jaws 4 and 6, and the angle of divergence between them, are not determined purely by the geometry of the apparatus, but also by the resistive properties of the tissues being manipulated. This results from the inherent flexibility of the jaw piece, e.g., leaves 62 and 64. When a thick or tough bit of tissue is grasped, it is possible to squeeze members 14 and 16 all the way together without causing jaws 4, 6 to close fully on one another so as to damage the tissue disposed between them. Instead, due to the resistance offered by the tissue being manipulated and the resiliency of the leaves 62 and 64, jaws 4 and 6 may remain partially open and at some angle of divergence, without however relinquishing a firm grip on the tissues between them. In other words, the arrangement of parts in the apparatus of the invention is such that it is forgiving of excessive force as applied by the surgeon to handle members 14 and 16. The force actually applied to the tissues is limited by the spring rate of leaves 62, 64 which can be varied to meet precisely the requirements of the particular surgical application for which the apparatus is intended. Similarly, the apparatus is relatively insensitive to the thickness of the tissues being manipulated. Thus handle members 14 and 16 may be fully contracted, whereby the tissues may be held securely by the jaws, even though the tissue is so thick that the jaws cannot close completely.

In the preferred embodiment of the apparatus, outer tube 8 is made wholly or partially (and particularly where it envelops jaws 4 and 6) of a material such as polytetrafluorethylene or PTFE, which is available from DuPont and sold under the trademark Teflon. Such material has extremely low and nearly equal coefficients of static and sliding friction when mated with jaws 4 and 6 when the latter are made of a polished metal. This ensures that relatively little force is needed to translate outer tube 8 over jaws 4 and 6, notwithstanding the resistive force offered by jaws 4, 6 (and their contents) to movement of outer tube 8. Due to the acuteness of the angle of divergence between jaws 4 and 6, in a substantially frictionless or low friction embodiment of the apparatus, a relatively small amount of translational force applied to outer tube 8 is sufficient to urge closed even a relatively strong set of leaves 62, 64, and hence jaws 4, 6. If outer tube 8 is made of PTFE and jaws 4, 6 of polished spring steel, the apparatus approaches the frictionless ideal, with the result that the mechanical advantage of the apparatus is enhanced.

Leaves 62 and 64 are capable of back-driving or forcing outer tube 8 rearward (thereby allowing the jaws to reopen) unless outer tube 8 has progressed forward sufficiently far to cover the inflection where leaves 62, 64 merge with jaws 4, 6. Thereafter, although outer tube 8 continues to translate easily over jaws 4, 6 the latter may no longer be able to feed their expansive force back to outer tube 8 so as to urge it rearward, the reason being that no longer is the interface between outer tube 8 and jaws 4, 6 at an acute angle to the axis of the apparatus. Instead, the forces at said interface act radially or at right angles to the axis of outer tube 8. Consequently, outer tube 8 tends to remain where it is placed. Thus, until jaws 4, 6 are substantially closed (or as closed as they can be when resistive tissues are being grasped), leaves 62, 64 act as return springs resisting the surgeon's contractile finger effort. After jaws 4, 6 are fully enveloped by outer tube 8, as shown in FIG. 2, whether or not the jaws themselves are partially held open by the tissues between them, the return spring action ceases and an inherent locking-in-place action obtains.

Referring again to FIGS. 1-5, because PTFE and some other suitable materials for outer tube 8 may not have enough strength to resist deformation by the radial forces that leaves 62, 64 exert upon outer tube 8, it may be desirable to place a rigid sleeve 66 firmly over the distal end of outer tube 8. Sleeve 66 is preferably made of a material, such as stainless steel, having a relatively high modulus of elasticity. As a result, sleeve 66 prevents any substantial deformation of outer tube 8. This is true even if the wall thickness of sleeve 66 is relatively small, so that sleeve 66 need not increase unduly the diameter of the apparatus. As an alternative measure, tube 8 may be provided with a reduced diameter front end to accommodate sleeve 66 and the latter may have an o.d. equal to that of tube 8, so as to eliminate any surface discontinuities.

Figure 21:
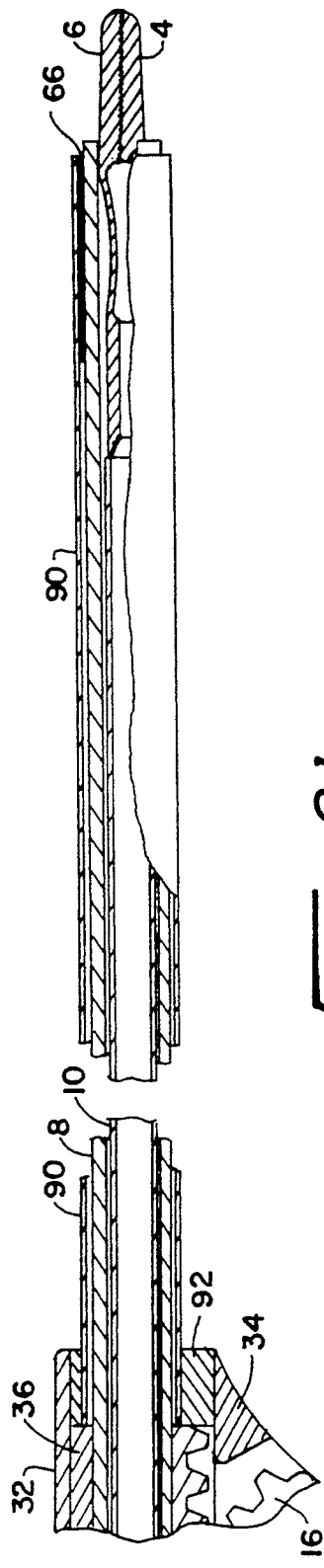
FIG. 21 is a longitudinal sectional view in side elevation of an embodiment similar to the one shown in FIG. 2 that includes an outer sheath.

Referring now to FIG. 21, although jaw piece 2 does not move longitudinally relative to stationary handle member 16 as the apparatus is used, outer tube 8 does so move, and therefore it may also move with respect to the tissue surrounding the incision through which the apparatus enters the body of the patient undergoing surgery. Therefore, in surgical circumstances where relative motion between outer tube 8 and the tissue surrounding the incision (or between outer tube 8 and a cannula interposed between the tissue surrounding the incision and the apparatus of this invention) is intolerable or undesirable, it may be advantageous to enclose outer tube 8 in a loosely fitting protective tube 90 (FIG. 21), rigidly secured (as by press fitting) on the inner diameter of a plug 92 that is secured to housing 34. Tube 90 is radially spaced from outer tube 8 as shown in FIG. 21. Protective tube 90 may have the same outer diameter as sleeve 66, provided that protective tube 90 is sufficiently short that it can never butt against sleeve 66, regardless of the positioning of tube 8. In this case, the surrounding tissues, if any, may be exposed to the movement of only that portion of outer tube 8 that is not enclosed by protective tube 90.

The instrument of the invention provides an unobstructed passage along its axis in the form of the internal bore through which ancillary devices may be passed, e.g., a laser-conducting optical fiber light guide, a cauterizing device, and the like. As shown in FIGS. 2 and 3, this bore may commence at rear surface 100 of stationary housing member 34 where the rear end of inner tube 10 has its opening 102 flush with surface 100. Alternatively, inner tube 10 may be extended rearward and, if desired, equipped with any well known connector means to facilitate attaching a hose or tube for conducting fluids through the apparatus, e.g., for irrigation or aspiration purposes, and also for attaching a source of electrical power for electrosurgery. Also the rear termination of inner tube 10 may be machined or otherwise modified to accommodate various ancillary devices which require threaded or other attachment means. In any case, the axial bore of tube 10 continues forward for the entire length of that tube to where it abuts and is joined to jaw piece 2. Hole 60 of jaw piece 2 may be larger than, the same size as, or smaller than the inside diameter of inner tube 10. In the event hole 60 is smaller in diameter than the passage in tube 10, the transitional taper surface 24 eases the passage of an ancillary device past the junction of inner tube 10 and jaw piece 2. It should be noted that although leaves 62, 64 may, when in certain possible positions, such as the position shown in FIG. 2, assume a concave or hourglass shape with respect to each other, nevertheless at their point of closest approach the space between leaves 62, 64 is still large enough to admit at least partial passage of an ancillary device in hole 60.

As previously discussed, there is an inherent locking effect that obtains when outer tube 8 has been translated fully forward and therefore maximally envelops jaws 4, 6. It also may be desirable to have the ability to lock jaws 4, 6 in any possible position regardless of the position of tube 8. As shown in FIGS. 1-7, the preferred embodiment may be equipped with a locking lever 110 which is firmly secured to pivot pin axle 18. The exterior of locking lever 110 can have a variety of shapes. The shape illustrated in the FIGS. 1-7 is designed for thumb operation by a right-handed surgeon. Clearly, a similar lever can be provided on the opposite side of the apparatus for convenient use by a left-handed person, although this will require that the thread 112 (see FIGS. 6, 7) on the axle 18, as well as thread 114 on the boss 116, be a left-hand thread. Furthermore, for a left handed version boss 116 would be relocated to the opposite side of housing 34. Alternatively, if axle 18 is extended outward a substantial distance beyond the outer face of boss 116, locking lever 110 as shown in the FIGS. 1-7 can be supplemented by a second locking lever that is a mirror image of locking lever 110. Said second locking lever may be immovably secured to said extension of axle 18 so as to make use of the locking provision of the apparatus ambidextrous.

It is obvious from FIGS. 2 and 6, which show locking lever 110 in the locked position, and FIG. 7, which shows it in the unlocked position, that the operating arc through which locking lever 110 rotates is relatively small. It is also evident that the shape of thumb surface 118 of locking lever 110 may be shaped to permit the surgeon's thumb to move locking lever 110 in either rotational direction without the need for the surgeon to shift his grip on the apparatus (see FIG. 2). Thumb surface 118 is preferably smooth, rather than serrated, so that the thumb can slide freely and comfortably along thumb surface 118 as the operating arc of locking lever 110 is traversed. Many other ergonomic arrangements, such as variations in the shape and rotational direction of locking lever 110, will be envisioned by those skilled in the art, and are understood to fall within the scope of the present invention.

The operation of locking lever 110, in the preferred embodiment of the invention, depends on friction, although obviously a ratchet or other means also might be employed. As seen most clearly in FIGS. 6, 7 and 8, movable handle member 14 rotates within a slot 120 in stationary handle member 16. This slot 120 is bounded laterally by side walls 122 and 124 of stationary handle member 16. The gap between side walls 122 and 124, i.e., the slot width, is slightly greater than the thickness of that portion of movable handle member 14 which is located between side walls 122 and 124. FIG. 7 shows the apparatus unlocked, with movable handle member 14 free to rotate between side walls 122 and 124 of stationary member 7.

In FIG. 6, locking lever 110 has been rotated clockwise (as viewed in FIG. 2) to its fully locked position. This action has caused the right-hand male screw threads 112 of axle 18 to advance along the mating female screw threads 114 (FIG. 7) in boss 116 of side wall 124 of stationary handle member 16, thereby enabling shoulder 126 of locking lever 110 to squeeze side walls 122 and 124 together, capturing by friction that portion of movable handle member 14 that lies between side walls 122, 124. It is obvious that the amount of locking action is progressive and is regulated by the angle through which locking lever 110 is rotated from its unlocked position. As described in more detail hereafter, locking lever 110 is installed on axle 18 in such an angular orientation that the locking action begins almost immediately after locking lever 110 is rotated away from its unlocked position stop. This stop position is shown in the FIGS. 2, 5 and 6 as comprising protuberance 128 integral with stationary handle member 16. The locking action becomes progressively more pronounced until locking lever 110 has attained approximately the position shown in FIG. 2, which represents the fully locked position and corresponds to the maximum force the surgeon can apply comfortably to locking lever 110. Thus, no mechanical limit stop is needed in the locking direction of locking lever 110, although a second protuberance similar to protuberance 128 could easily be incorporated into stationary handle member 16 for that purpose. In the preferred embodiment, said second protuberance has been omitted for reasons of comfortable gripping of the apparatus as well as the absence of need for it, although some surgeons may wish to have a positive full-lock stop in order to avoid the possibility of over-tightening screw threads 112.

In the fully locked condition of the apparatus (see FIG. 2), the locking action is sufficiently strong to lock jaws 4, 6 securely in whatever position is desired by the surgeon. In intermediate conditions between fully locked and fully unlocked, a selectable amount of frictional drag is possible according to the surgeon's preferences. It should be observed that the frictional locking effect might be augmented by providing mating male and female radial serrations or ridges on side walls 122, 124 and movable handle member 14, which might also impart a ratcheting feel to the partially locked apparatus.

The squeezing together of side walls 122, 124 as locking lever 110 is rotated toward its fully locked position, thereby advancing screw threads 112 of axle 18 into boss 116 of stationary handle member 16, requires that shoulder 126 of locking lever 110 apply force against left side wall 122, urging it toward side wall 124. This cannot occur unless locking lever 110 is immovably attached to axle 18. Otherwise, locking lever 110 might slip on axle 18 and prevent said squeezing action. The attachment of locking lever 110 to axle 18 can take many forms. As shown in FIGS. 6 and 7, locking lever 110 is tightly press fitted over knurls or flutes 130 on axle 18. Knurls 130, and the mating hole in locking lever 110, are so configured that neither axial nor radial movement between axle 18 and locking lever 110 is possible under operating conditions once they are pressed together. The choice of straight knurls, instead of many other possible attachment methods obvious to those skilled in the art, is based on practical considerations.

For rapid assembly of the apparatus, axle 18 can be screwed into boss 116 until the end of axle 18 is flush with the outer face 132 of boss 116. Thereafter, locking lever 110 can be positioned rotationally so that it is in the fully locked attitude as shown in FIG. 2, and, being held in that orientation, can be pressed hard onto axle 18 until it is stopped by the full compression of side wall 122 against movable handle member 14, and the latter in turn against side wall 124. Following the pressing operation as just described, the apparatus is in the fully locked condition, locking lever 110 is correspondingly in its fully locked position, and upon counterclockwise rotation of locking lever 110 toward protuberance 128, the apparatus will unlock and be ready for use, and thereafter the lock will perform as described above.

As seen in FIGS. 6 and 7, a spring washer 134 and a flat washer 136 may be interposed between shoulder 126 of locking lever 110 and left side wall 122 of stationary handle member 16. The purpose of flat washer 136 is to prevent scoring of stationary handle member 16, which may be made of a much softer material than spring washer 134. The function of spring washer 134 is to provide frictional resistance against the rotation of locking lever 110, to prevent rattling or unintended rotation of locking lever 110 when it is not in its fully locked position, and also to provide locking lever 110 with an instrument-like feel. Locking lever 10 may be provided with a detent (not shown) that restrains it in the unlocked position.

It will be observed (see FIGS. 6 and 7) that the smooth shank central portion 138 of axle 18 is loosely fitted to a bushing 140 having a length slightly less than the thickness of the surrounding portion of movable handle member 14. It is envisioned that movable handle member 14 may be fabricated of a relatively soft plastic material, in which case shank 138 might tend, after protracted operation of the apparatus, to wear oversize an unbushed hole in movable handle member 14. Bushing 140, which is made of a relatively hard material, is intended to prevent such wear. Bushing 140 is pressed into movable handle member 14, so that any rotational motion of movable handle member 14 is relative to axle 18 rather than to bushing 140. Bushing 140 may be superfluous where the instrument is intended to be used once and then disposed.

The apparatus may be constructed without provision for a locking lever (see FIG. 8). In this case, screw 142 takes the place of axle 18. The length of a bushing 144 is made equal to the width of the slot 120 in stationary handle member 16 bounded by side walls 122, 124, and spring washer 134 is eliminated. When screw 142 is fully tightened, side walls 122, 124 bear against the faces of bushing 140. Since bushing 140 is longer than the thickness of adjacent movable handle member 14, the latter remains free to rotate and no locking action is provided, except the inherent locking action of outer tube 8 enveloping jaws 14.

Figure 22:
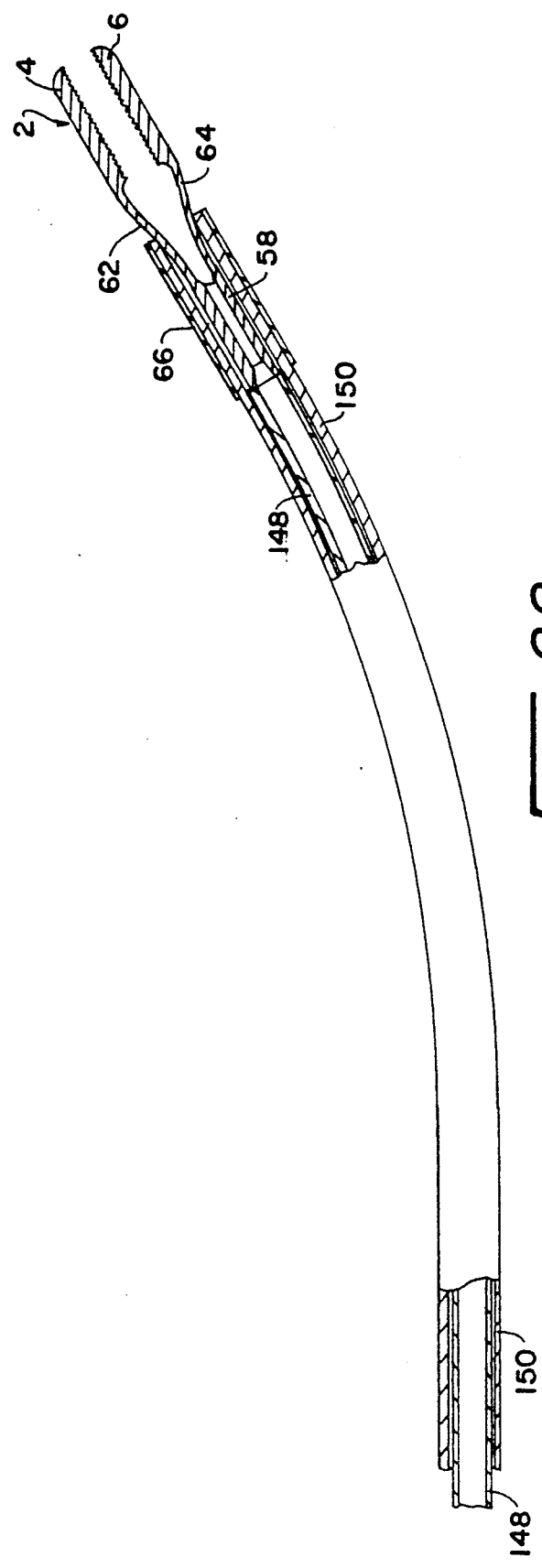
FIG. 22 is a fragmentary side view in elevation, partly in section, of an embodiment similar to the one shown in FIG. 2, except that the shaft is curved.

Referring now to FIG. 22, since outer tube 8 preferably is made of a flexible material such as PTFE, it is a simple matter to provide an instrument with a curved shaft. In this embodiment of the invention, inner tube 148 is bent to the desired curvature, and outer tube 150 (due to the low coefficients of friction and low modulus of elasticity of PTFE material) assumes the same curvature and slides easily over inner tube 148. Ancillary devices which are intended to pass through the apparatus must also be capable of conforming to the curvature of inner tube 148. It is also possible to fabricate inner tube 148 as a flexible member, such as a tightly-wound coil spring or a spiral-wound tube like a flexible electrical conduit, so that the entire shaft of the apparatus can be bent to the desired shape at the time of use. If inner tube 148 is made as a tightly-wound coil spring, it will maintain its curvature only while being held in that position. If inner tube 148 is made similarly to a spiral-wound electrical conduit, the shaft will remain substantially as bent, even after it is released by the surgeon.

Economic advantages of the apparatus of the invention are that there are relatively few parts, and they are easily manufactured of low-priced materials. Additionally, assembly is simple and straightforward and the parts are, in most cases, suitable for molded plastic fabrication. Consequently, the apparatus can be made as a disposable item at low cost. Further, manufacturing tolerances are relatively loose, effecting further economies.

It is obvious that the present invention is useful for various surgical applications, so that it is by no means limited to the specific applications and uses herein described, and that a wide variety of ancillary devices may be inserted into the jaw piece in the manner previously described. Furthermore, it is clear that various modifications may be made while still providing an apparatus which comes within the spirit and scope of the invention. For example, the jaw piece may be narrowed or curved in one or more dimensions so that the tool may function as a needle holder. Also, the jaw piece may be in the form of a triple equiangularly-spaced jaws and leaves. Additionally, since use of an instrument having inner and outer tubes will result in wearing the circular interior surface by repeated manipulation of some ancillary devices, the inner tube may be initially formed with a square hole.

What is claimed is:

1. A surgical instrument comprising:
   a housing provided with an internal bore, and at least first and second concentrically arranged tubular elements extending longitudinally away from said housing, said first tubular element having proximal and distal ends and being affixed at its proximal end so as to be immobile with respect to said housing, and said second tubular element surrounding said first tubular element and being arranged to translate longitudinally with respect to said first tubular element;
   translation means for causing said second tubular element to translate longitudinally relative to said first tubular element, said translation means comprising a stationary handle member and a movable handle member pivotally secured to said stationary handle member, and means on said movable handle member for engaging means affixed to said second tubular element for translating said second tubular element relative to said first tubular element in response to relative movement of said handle members, said means affixed to said second tubular element comprising a gear rack provided with a series of teeth, and said means on said movable handle member comprising at least a toothed gear member in engagement with the teeth of said gear rack, said housing also having means for limiting movement of said gear rack in the forward and reverse direction; and
   a jaw piece affixed to said distal end of said first tubular element, said jaw piece being an integral structure comprising at least two jaws which are biased and normally deployed away from one another, a rear section, and intermediate leaf spring elements connecting each of said jaws to said rear section, said second tubular element being arranged to slide over said two jaws, whereby when said second tubular element is caused to translate towards the distal end of said first tubular element, said second tubular element will slide over said jaw piece and cause said jaws to close towards one another.

2. The instrument of claim 1 wherein each of said intermediate leaf spring elements is configured to provide a convex curvature at its joinder with said rear section and a concave curvature at its joinder with its respective jaw.

3. The instrument of claim 1 wherein said rear section of the jaw piece has a hole extending through and communicating at one end with the interior of said first tubular element and at its other end to the space between said jaws, thereby permitting an ancillary device to be extended through said first tubular element to the jaws.

4. The instrument of claim 1 wherein said housing has a distal end and a proximal end, and the proximal end of said first tubular element terminates at the proximal end of said housing, thereby adapting said instrument for introduction of an ancillary device.

5. A surgical instrument comprising:
a housing provided with an internal bore, and at least first and second concentrically arranged tubular elements extending longitudinally away from said housing, said first tubular element having proximal and distal ends and being affixed at its proximal end so as to be immobile with respect to said housing, and said second tubular element surrounding said first tubular element and being arranged to translate longitudinally with respect to said first tubular element;
translation means for causing said second tubular element to translate longitudinally relative to said first tubular element; and
a jaw piece affixed to said distal end of said first tubular element, said jaw piece being an integral structure comprising at least two jaws which are biased and normally deployed away from one another, a rear section, and intermediate leaf spring elements connecting each of said jaws to said rear section, said second tubular element being arranged to slide over said two jaws, whereby when said second tubular element is caused to translate towards the distal end of said first tubular element, said second tubular element will slide over said jaw piece and cause said jaws to close towards one another; said translation means comprising a stationary handle member and a movable handle member pivotally secured to said stationary handle member, and means on said movable handle member for engaging means affixed to said second tubular element for translating said second tubular element relative to said first tubular element in response to relative movement of said handle members; and
means for selectively locking said movable handle member to said stationary handle member to retain the jaws in a selected position determined by translation of said second tubular element relative to said first tubular element.

6. The instrument of claim 5 wherein the portion of said stationary handle member to which said movable handle member is pivotally secured is bifurcated, and said movable handle member has a tongue section extending into the bifurcated portion of said stationary handle member, said movable handle member being rotatable about a pivot axis extending through said tongue section and said bifurcated portion of said stationary handle member.

7. The instrument of claim 6 further wherein said pivot axis is a pivot pin that projects from one side of said stationary handle member, and further including a locking lever rotatably attached to said pivot pin, and threaded means on said pivot pin and said stationary handle member, wherein when said locking lever is rotated relative to said pivot pin in a given direction, said bifurcated portion of said stationary handle member is compressed so as to hold said movable handle member against further movement.

8. A surgical instrument comprising;
a housing provided with an internal bore, and at least first and second concentrically arranged tubular elements extending longitudinally away from said housing, said first tubular element having proximal and distal ends and being affixed at its proximal end so as to be immobile with respect to said housing, and said second tubular element surrounding said first tubular element and being arranged to translate longitudinally with respect to said first tubular element;
translation means for causing said second tubular element to translate longitudinally relative to said first tubular element; and
a jaw piece affixed to said distal end of said first tubular element, said jaw piece being an integral structure comprising at least two jaws which are biased and normally deployed away from one another, a rear section, and intermediate leaf spring elements connecting each of said jaws to said rear section, said second tubular element being arranged to slide over said two jaws, whereby when said second tubular element is caused to translate towards the distal end of said first tubular element, said second tubular element will slide over said jaw piece and cause said jaws to close towards one another;
each of said jaws being provided with a groove located so as to be in alignment with said first tubular element when said jaws are in a closed position, thereby providing a passage extending from the exterior of said housing through said first tubular element and said jaw piece for introduction of an ancillary device even when said jaws are closed.

9. The instrument of claim 8 in which said jaw piece comprises a rear section having a hole extending axially therethrough and each of said jaws is connected to said rear section by an intermediate spring leaf element.

10. The instrument of claim 9 wherein each said intermediate leaf spring element is configured to provide a convex curvature at its joinder with said rear section and a concave curvature at its joinder with its respective jaw, whereby when said jaws are drawn into closed position so as to grasp tissue which is being addressed, the forward ends of said jaws close on one another before the rear ends of said jaws, whereby there is an absence of forward motion of said jaws so as to reduce trauma to the grasped tissue regardless of the positioning of said jaws.

11. A surgical instrument comprising:
a housing provided with an internal bore, and at least first and second concentrically arranged tubular elements extending longitudinally away from said housing, said first tubular element having proximal and distal ends and being affixed at its proximal end so as to be immobile with respect to said housing, and said second tubular element surrounding said first tubular element and being arranged to translate longitudinally with respect to said first tubular element;
translation means for causing said second tubular element to translate longitudinally relative to said first tubular element; and
a jaw piece affixed to said distal end of said first tubular element, said jaw piece being an integral structure comprising at least two jaws which are biased and normally deployed away from one another, a rear section, and intermediate leaf spring elements connecting each of said jaws to said rear section, said second tubular element being arranged to slide over said two jaws, whereby when said second tubular element is caused to translate towards the distal end of said first tubular element, said second tubular element will slide over said jaw piece and cause said jaws to close towards one another;

one of said jaws having a cutting blade attached thereto that extends substantially parallel to the axes of said tubular elements, and the other of said jaws having a groove for receiving said cutting blade.

12. A surgical instrument comprising:

a housing provided with an internal bore, and at least first and second concentrically arranged tubular elements extending longitudinally away from said housing, said first tubular element having proximal and distal ends and being affixed at its proximal end so as to be immobile with respect to said housing, and said second tubular element surrounding said first tubular element and being arranged to translate longitudinally with respect to said first tubular element;

translation means for causing said second tubular element to translate longitudinally relative to said first tubular element;

a jaw piece affixed to said distal end of said first tubular element, said jaw piece being an integral structure comprising at least two jaws which are biased and normally deployed away from one another, a rear section, and intermediate leaf spring elements connecting each of said jaws to said rear section, said second tubular element being arranged to slide over said two jaws, whereby when said second tubular element is caused to translate towards the distal end of said first tubular element, said second tubular element will slide over said jaw piece and cause said jaws to close towards one another;

a sheath affixed to the forward end of said housing and surrounding and protecting said second tubular element, said sheath extending longitudinally with said second tubular element, whereby when said instrument is placed into an incision and said instrument is operated so as to cause said second tubular element to translate within said housing, said second tubular element will translate within said sheath so as not to cause trauma to the patient.

13. A surgical instrument comprising:

a housing provided with an internal bore, and at least first and second concentrically arranged tubular elements extending longitudinally away from said housing, said first tubular element having proximal and distal ends and being affixed at its proximal end so as to be immobile with respect to said housing, and said second tubular element surrounding said first tubular element and being arranged to translate longitudinally with respect to said first tubular element;

translation means for causing said second tubular element to translate longitudinally relative to said first tubular element;

a jaw piece affixed to said distal end of said first tubular element, said jaw piece being an integral structure comprising at least two jaws which are biased and normally deployed away from one another, a rear section, and intermediate leaf spring elements connecting each of said jaws to said rear section, said second tubular element being arranged to slide over said two jaws, whereby when said second tubular element is caused to translate towards the distal end of said first tubular element, said second tubular element will slide over said jaw piece and cause said jaws to close towards one another;

said first tubular element having a curved configuration, and said second tubular element being made of a material that enables it to assume the same curvature as said first tubular element as it undergoes translational movement.

14. A surgical instrument for grasping objects at a remote location comprising:

a housing;

first and second concentrically arranged longitudinally extending tubes, said first tube having proximal and distal ends and being fixed at said distal end to said housing, and said second tube surrounding said first tube and being arranged to translate longitudinally with respect to said first tube;

a unitary preformed jaw piece having at least two jaws, a rear section, and intermediate spring leaf elements connecting each jaw to said rear section, said spring leaf elements being arranged so as to normally bias and deploy said jaws so that they are in an open position relative to one another, whereby when said second tube is caused to translate towards the distal end of said first tube, said second tube will overlap said jaw piece and cause said jaws to close towards one another, each intermediate leaf spring element being configured so as to provide a convex flexure at its joinder with said rear section and a concave flexure at its joinder with its respective jaw.

15. The instrument of claim 14 wherein said rear section of said jaw piece has a hole extending through and communicating at one end with the interior of said first tube and at its other end to the space between said jaws, thereby permitting any device which is extended through said first tube to be presented at the space between the jaws.

16. The instrument of claim 14 including operating means for causing said second tube to move longitudinally relative to said first tube, said translation means comprising a stationary handle member and a movable handle member pinned to said stationary handle member for rotational movement with respect thereto, and means on said movable handle member for engaging means affixed to said second tube for moving said second tube longitudinally relative to said first tube in accordance with the relative positioning of said handle members.

17. The instrument of claim 16 including means for selectively locking the movable handle member to said stationary handle member.

18. The instrument of claim 16 wherein said stationary handle member has a bifurcated section, and said movable handle member has a section that extends into and is pivotally secured to the bifurcated section of said stationary handle member.

19. The instrument of claim 14 having two elongate jaws that extend lengthwise of said tubes, and further wherein said jaws are each provided with a groove so located that when said jaws are in closed position said grooves confront one another and are in alignment with said first tube.

20. The instrument of claim 14 including a sheath surrounding and protecting said second tube but being spaced therefrom, said sheath extending longitudinally with said second tubular element away from said housing;

whereby when said second tube translates longitudinally with respect to said first tube it will translate within said sheath and not subject said second tube to ambient conditions.

21. The tool of claim 14 wherein said first tube is of curved configuration, and said second tube is made of a material that enables it to assume the same curvature as said first tubular element as it translates thereover.

22. A surgical instrument for grasping objects at a remote location comprising:

first and second concentrically arranged longitudinally extending tubes, said first tube having proximal and distal ends and being fixed with respect to said second tube, and said second tube surrounding said first tube and being arranged to translate longitudinally with respect to said first tube;

a unitary jaw piece comprising a rear section affixed to said first tube at its distal end, at least two jaws, and intermediate spring leaf elements each connecting one of said jaws to said rear section and acting to bias said jaws away from one another to an open position, whereby when said second tube is caused to translate towards the distal end of said first tube, said second tube will overlap said jaw piece and cause said jaws to close towards one another;

operating means for causing said second tube to move longitudinally relative to said first tube, said translation means comprising a stationary handle member and a movable handle member pinned to said stationary handle member for rotational movement with respect thereto, and means on said movable handle member for engaging means affixed to said second tube for moving said second tube longitudinally relative to said first tube in accordance with the relative positioning of said handle members; and said operating means comprises a gear rack provided with a series of teeth attached to said second tube, and a toothed element attached to said movable handle member in engagement with the teeth of said gear rack.

23. The instrument of claim 22 further including means for limiting movement of said second tube relative to said first tube.

24. A surgical instrument comprising:

a housing provided with an internal bore;

first and second elongate elements extending longitudinally away from said housing, said first element having proximal and distal ends with said distal end being furthest from said housing, said proximal end of said first element extending into said bore and being affixed to said housing, and said second element being a tubular shaft having proximal and distal ends corresponding to their relative positions to the proximal and distal ends of said first element, said second element concentrically surrounding said first element and being arranged to translate longitudinally with respect to said first tubular element;

translation means for causing said second element to translate longitudinally relative to said first element, said translation means comprising a stationary handle member formed integral with said housing, a movable handle member pivotally secured to said stationary handle member, and means on said movable handle member for engaging means affixed to said second element for translating said second tubular element relative to said first element in response to relative movement of said handle members; and a jaw piece in the form of an integral one-piece structure comprising at least two jaws, a rear section affixed to said distal end of said first element, and intermediate leaf spring elements connecting each of said jaws to said rear section, and biasing said jaws away from one another;

said second element being arranged to slide over said two jaws when said movable handle member is pivoted relative to said stationary handle member in a predetermined direction, whereby said second element will engage said leaf spring element and thereby force said jaws to close on one another.

25. A surgical instrument according to claim 24 wherein said jaws have a distal end and a proximal end with the distal ends of said jaws being furthest from said housing, and said leaf spring elements are arranged so that when engaged by said distal end of said second element they will cause the distal ends of said jaws to close before the proximal ends of said jaws.

26. A surgical instrument comprising:

a housing (34) having an internal cavity;

first and second concentrically arranged tubular elements (10,8) extending longitudinally away from said housing, said first and second tubular elements each having a proximal end and a distal end, said proximal end of said first tubular element (10) extending into and being fixed to said housing, and said second tubular element (8) surrounding said first tubular element and being arranged to move longitudinally with respect to said first tubular element and said housing, said proximal end of said second tubular element extending into said cavity;

a preformed jaw piece (2) affixed to said distal end of said first tubular element, said jaw piece being an integral structure comprising a rear section (58) attached to the said distal end of said first tubular element, at least two jaws (4,6), and intermediate leaf spring elements (62,64) connecting each of said jaws to said rear section, said leaf spring elements biasing said jaws so that they are normally deployed away from one another;

first and second manually-engagable members (16,14) for holding and operating said instrument, said first manually-engagable member (16) being fixed to said housing and said second manually-engagable member (14) being movable relative to said first manually-engageable member and said housing; and means (36,38,40) providing a motion-translation connection between said second manually-engagable member (14) and said second tubular element (8) whereby bi-directional movement of said second manually-engageable member relative to said first manually-engagable member will cause said second tubular member to undergo bi-directional movement longitudinally relative to said first tubular element; and said second manually-engageable member being movable relative to said first manually-engagable member to an extent such as to cause said second tubular element to move longitudinally relative to said housing and said first tubular element towards the distal end of said first tubular element far enough for said distal end of said second tubular element to slide over said jaw piece and force said leaf spring elements toward one another so as to cause said jaws to close towards one another.

27. An instrument according to claim 26 wherein said motion translating connection comprises a gear rack (36) connected to and movable with said second tubular element, and gear teeth (38) on said second manually-engagable member engaged with said gear rack, whereby movement of said second manually-engagable member relative to said first manually-engagable member and said housing will cause said second tubular element to move longitudinally relative to said first tubular element.

28. An instrument according to claim 27 wherein said gear rack is disposed in said cavity.

29. An instrument according to claim 27 wherein said gear rack forms part of a hollow extension member that is attached to said proximal end of said second tubular element and slidably surrounds said first tubular element, and further including an O-ring disposed between said hollow extension member and said first tubular member so as to prevent fluids from migrating between said hollow extension member and said first tubular member.

30. An instrument according to claim 26 wherein each jaw has a distal end and a proximal end located closest to said housing, and further wherein said leaf spring elements are contoured so that when said second tubular element slides over said jaw piece, said leaf spring elements will be biased by said second tubular element so as to cause said jaws to close progressively starting with the distal ends of the jaws and then progressing toward the proximal ends of the jaws, whereby the proximal ends of said jaws will make contact last with any tissue disposed between the jaws.

* * * * *